United States Patent [19]

Nicholas et al.

[11] Patent Number: 4,761,167
[45] Date of Patent: Aug. 2, 1988

[54] HYDROCARBON RECOVERY FROM FUEL GAS

[75] Inventors: David M. Nicholas, New Tripoli; Thomas M. Roden, Macungie; Gerry N. Gottier, Allentown, all of Pa.

[73] Assignee: Air Products and Chemicals, Inc., Allentown, Pa.

[21] Appl. No.: 940,823

[22] Filed: Dec. 12, 1986

[51] Int. Cl.4 ............................................. F25J 3/00
[52] U.S. Cl. ........................................ 62/17; 55/25; 55/53; 55/62; 62/20
[58] Field of Search ............... 62/17, 18, 20; 55/25, 55/58, 62

[56] References Cited

U.S. PATENT DOCUMENTS

| | | | |
|---|---|---|---|
| 3,854,856 | 7/1975 | Lofredo et al. | 62/18 |
| 4,077,779 | 3/1978 | Sircar et al. | 55/25 |
| 4,158,556 | 6/1979 | Yearout | 62/17 X |
| 4,171,206 | 10/1979 | Sircar | 55/58 X |
| 4,311,495 | 1/1982 | Styring, Jr. | 62/17 |
| 4,411,677 | 10/1983 | Pervier et al. | 62/25 |
| 4,475,930 | 10/1984 | Asztalos | 55/62 X |
| 4,504,295 | 3/1985 | Davis et al. | 62/30 |
| 4,561,865 | 12/1985 | McCombs et al. | 55/25 |
| 4,578,089 | 3/1986 | Richter et al. | 55/58 X |

FOREIGN PATENT DOCUMENTS 2154465 2/1985 United Kingdom ............... 55/25

OTHER PUBLICATIONS

Oil & Gas Journal, "Dome's NRU is Successfully Treating Gas from an EOR Project", by Alvarez, M. R. et al., published Aug. 20, 1984 at pp. 95–99.

Primary Examiner—Steven E. Warner
Attorney, Agent, or Firm—Geoffrey L. Chase; William F. Marsh; James C. Simmons

[57] ABSTRACT

High purity methane is recovered from a fuel gas stream containing the same in admixture with mainly nitrogen and carbon dioxide, by first removing the carbon dioxide by selective adsorption in a PSA system and separating the remaining nitrogen from the methane by cryogenic distillation, the rejected nitrogen being employed for purging the $CO_2$-laden adsorbent beds of the PSA system. Cyclic regeneration of the sorbent-laden bed may entail nitrogen purge with or without including a carbon dioxide rinse, or the nitrogen purge of the sorbent-laden bed may be used in combination with pressure let-down by gas withdrawal into one or more companion beds.

8 Claims, 4 Drawing Sheets

HYDROCARBON RECOVERY FROM FUEL GAS

TECHNICAL FIELD

The present invention is concerned with recovery of methane from fuel gas streams.

BACKGROUND OF THE INVENTION

Fuel gas streams obtained from various sources usually contain, in addition to methane and other combustible hydrocarbons, substantial quantities of carbon dioxide and nitrogen. A typical mixed gas stream, such as that obtained from enhanced oil recovery (EOR) operation may contain in addition to methane, in the order of about 50% or more of non-combustible gases (such as $N_2$ and $CO_2$). To recover the methane in purified form from such gas mixtures the conventional processes employ a chemical solvent, such as monoethanolamine, to separate accompanying components from the desired methane. In typical prior art operation, for example, the crude off-gas is subjected to cryogenic distillation, whereby most of the $C_2+$ hydrocarbons and part of the carbon dioxide are separated. The remaining gas fraction is treated with the chemical solvent to extract the bulk of the remaining $CO_2$ and the separated crude methane product is subjected to drying and refrigeration to remove water and residual $CO_2$. The nitrogen remaining is removed from the resulting product in a Nitrogen Rejection Unit (NRU), such as that described in U.S. Pat. Nos. 4,411,677 and 4,504,295 and in a paper by Alvarez, M. R., et al., published in Oil and Gas Journal, Aug. 20, 1984 at pages 95-99.

In these conventional processes employing chemical solvent for $CO_2$ removal from fuel gas, the gas driers and the refrigeration systems required represent major capital and operating expenses. Moreover, the use of such chemical solvent systems to remove the carbon dioxide is an energy intensive process requiring steam to regenerate the solvent.

The separation of methane from gas mixtures containing also carbon dioxide by PSA operation, is disclosed in prior art patents. Among these, for example, U.S. Pat. No. 4,077,779 discloses a PSA system generally applicable to bulk separation of various gas mixtures, including the separation of $CO_2$ from its admixture with methane, in a six step cycle, wherein following selective adsorption of one of the components of the mixture, the adsorbent bed is rinsed with part of the adsorbed component at superatmospheric pressure. The pressure in the rinsed bed is lowered to an intermediate level to desorb the same, the withdrawn gas in this step being employed in the high pressure rinse step. The bed is next purged with an extraneous gas (air or inert) and then evacuated to remove the purge gas, following which the bed is brought back to superatmospheric pressure level for repetition of the cycle.

Among the objects of the present invention is to provide a simpler and less costly system and process than that conventionally employed for recovery of methane from mixed gas streams containing the same.

SUMMARY OF THE INVENTION

Instead of the conventional practice employing a chemical solvent absorption unit coupled to refrigeration and drying means to remove carbon dioxide from a fuel gas stream, the present invention employs pressure swing adsorption (PSA). Nitrogen is removed from the resulting PSA product stream in a Nitrogen Rejection Unit (NRU) and the nitrogen is beneficially utilized to regenerate the adsorbent in the PSA beds. Thus, in contrast to the prior art solvent system, no external heat source is needed to generate steam for regeneration. Also, the prior art need for a refrigeration/drier system to remove components subject to freezing ($CO_2$ and $H_2O$) in the NRU is avoided, since in the novel PSA systems of the present invention all of the water and $CO_2$ are removed from the fuel gas stream before its introduction into the NRU.

DETAILED DESCRIPTION

The process of the invention, while not limited thereto, may be advantageously employed for recovery of methane from mixed gas streams containing the same accompanied by $CO_2$ and nitrogen. Such mixed gas streams are had, for example, where the crude gas from enhanced oil recovery operation with $CO_2$ is subjected to cryogenic distillation, yielding a fuel gas composition generally containing 50 to 80 mole% $CH_4$ and 20 to 50% nitrogen and $CO_2$, and may contain trace amounts of higher boiling hydrocarbons.

Figure 1:
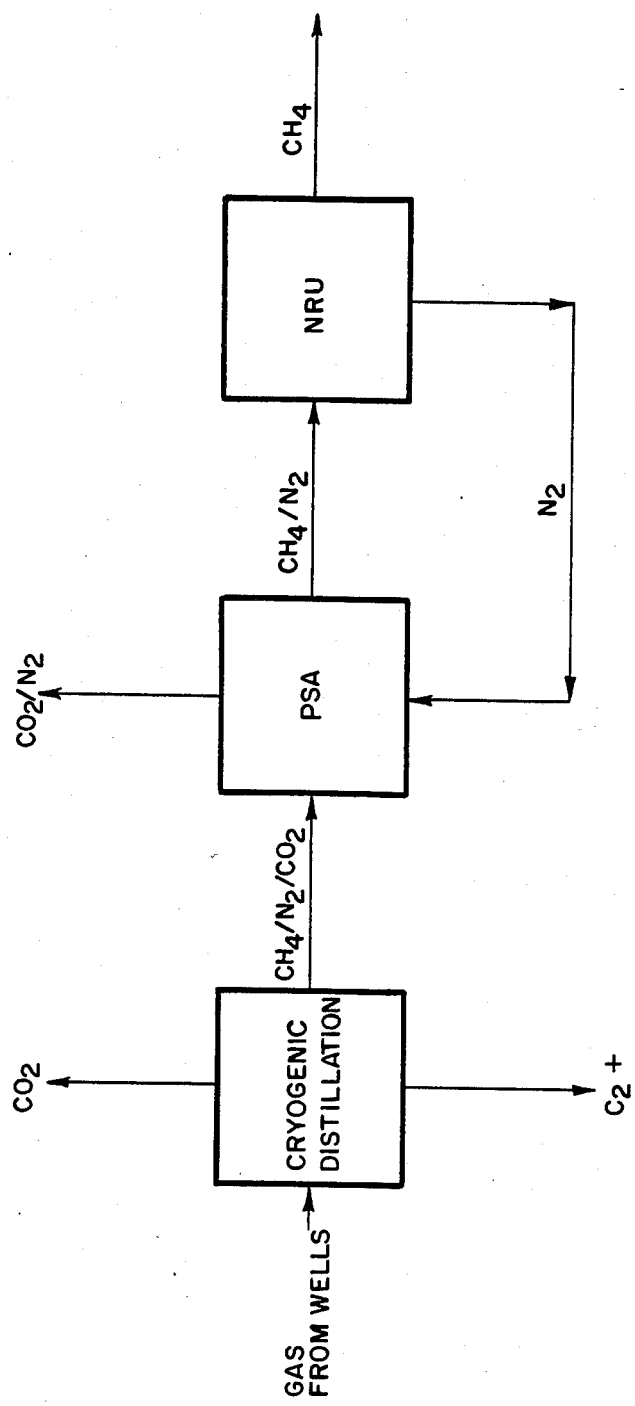
FIG. 1 is a simplified block flow diagram of the process according to the invention.

As illustrated in the flow diagram of FIG. 1, after removal of part of the $CO_2$ and most of the $C_2+$ hydrocarbons from the gas recovered from the well, the mixed gas composed chiefly of methane, nitrogen and $CO_2$ is introduced into a PSA system for removal of $CO_2$ by selective adsorption. The unadsorbed effluent comprised of methane and nitrogen is charged to a NRU, in which the nitrogen is separated and returned to regenerate the $CO_2$-laden adsorbent in the PSA beds, while the substantially pure methane is recovered for desired uses.

CASE I

Figure 2:
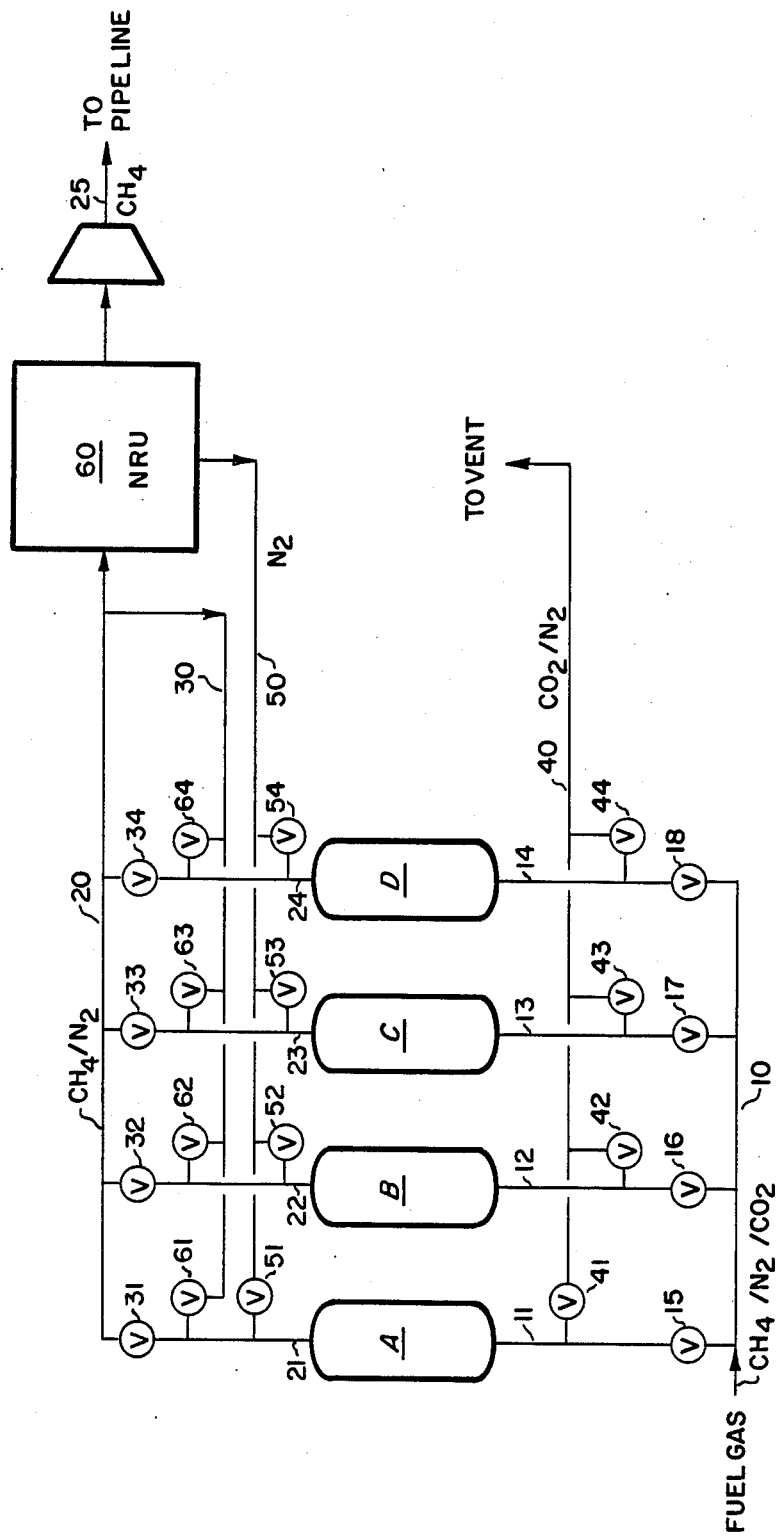
FIGS. 2 to 4 are more detailed flow diagrams of alternative systems for practice of the invention.

Various systems and arrangements can be employed in practice of the invention, the simplest of these is diagrammatically illustrated in FIG. 2, wherein four adsorption columns are employed, operated in parallel, in combination with the NRU unit. The PSA arrangement in FIG. 2 is designed for a four-step operating cycle, wherein each of the steps is performed during a substantially equal time period for (a) adsorption of $CO_2$, (b) depressurization of the column, (c) purge with nitrogen from the NRU and (d) repressure with unsorbed PSA effluent.

In operation of the FIG. 2 embodiment with mixed gas feed composed of methane, nitrogen and $CO_2$ (together with possible trace amounts of higher hydrocarbon and/or other substances), is supplied by manifold 10 to one of the columns A, B, C or D of the PSA system which is then onstream, through the appropriate connecting line 11, 12, 13 or 14. Assuming that column A is to be placed on-stream, valve 15 in line 11 is opened. Each of the columns contains a bed of adsorbent selective in the retention of $CO_2$ while less strongly adsorbed nitrogen and methane exit from the column into the associated one of the discharge lines 21, 22, 23, 24 connected to discharge manifold 20. Thus, with column A then on-stream, the unsorbed effluent is discharged via line 21 into manifold 20 through then open valve 31.

The mixed gas is manifold 20 is discharged into the associated NRU facility 60 in which the nitrogen is separated from the methane by fractional distillation. The methane is compressed and sent to the pipe line via line 25, while all or part of the nitrogen is utilized in regeneration of the $CO_2$-laden adsorbent of the PSA system as will hereinafter be described.

The described adsorption step is continued in column A for a predetermined fixed period short of breakthrough of $CO_2$ from the adsorbent bed therein. At the termination of the designed adsorption step valves 15 and 31 are closed and the feed from manifold 10 switched to another one of the columns then ready for adsorption.

The bed in column A, at the termination of the adsorption step is then subjected to regeneration. The column is depressurized in a direction counter to that of feed introduction by opening valve 41 through which gas from column A, comprised primarily of desorbed $CO_2$, and void space gas containing $CH_4$ and $N_2$, is discharged into line 40 and thereby vented.

When column A is at about atmospheric pressure of somewhat above, valve 51 is opened admitting nitrogen to flow into and through the column from the nitrogen rejection unit 60 via line 50, to discharge into line 40 via open valve 41.

Following purging with nitrogen, valves 41 and 51 are closed and column A is repressured with methane and nitrogen to substantially the superatmospheric pressure employed for the adsorption step. The repressurizing of column A is performed by opening valve 61 connecting the column to manifold 30, thereby withdrawing part of the gas being discharged into manifold 20 from a companion column then on-stream. Thus, if column D is then on adsorption, valves 18 and 34 being open, the unadsorbed effluent from line 24 flows into line 20 and will be split, with a preset part of the methane and nitrogen going to the NRU installation 60 with the remainder flowing into column A via lines 30 and 21 through open valve 61 to repressurize column A.

The operating cycle for the four column PSA system illustrated in FIG. 2 is set out in Table 1, assuming equal time periods for each of the steps of the operation.

Each of time periods I to IV may be in the order of about three or more minutes so that a complete cycle will occupy 12 or more minutes depending, among other considerations, upon the adsorptive capacity of the adsorbent bed in the column.

The PSA system removes most of the trace elements present in the feed gas in addition to removal of $CO_2$ so that the unadsorbed effluent sent to the NRU installation consists substantially of methane and nitrogen. With the removal of nitrogen at 60, a high purity methane stream is obtained. The use of all or part of the nitrogen as purge gas allows for additional methane recovery in the PSA system, since none of the methane need be used as sweep gas as typically required in conventional PSA systems.

The adsorption step in the above described four step cycle and in other alternative cycles hereinafter described may be carried out at a pressure in the range of greater than 100 psia. The depressurizing for desorption of $CO_2$ may be effected at lowest possible pressure, which may be in the order of about 20 psia. At this low pressure, nitrogen withdrawn from the NRU can be directly employed to purge the sorbed $CO_2$. In the system above described (four step operation) there is a small loss of methane product (~10%) in the void space gas purged by the nitrogen.

CASE II

Figure 3:
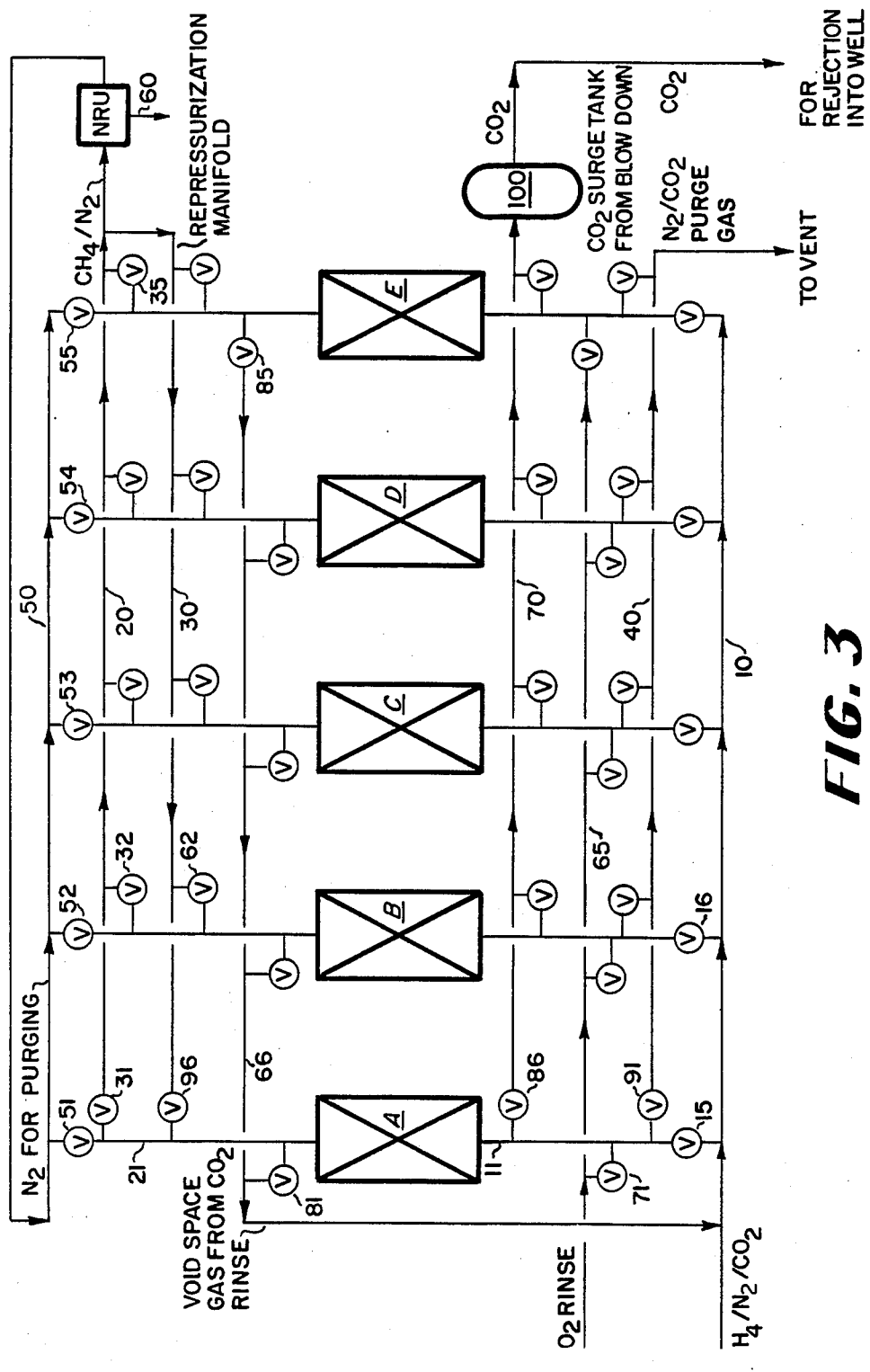

The system illustrated in FIG. 3 may be employed to advantage, since essentially all of the methane content of the feed gas is usefully recovered. In the system illustrated in FIG. 3, five adsorption columns are employed, operated in parallel. Following the adsorption of carbon dioxide from the feed gas, the $CO_2$-laden column is rinsed with $CO_2$, which may be such as that employed in well-injection gas used for EOR application. While each of the operating steps of the cycle may be set for an equal time period, such operation need not necessarily be followed. An operating schedule for a five column system employing an equal time period for each step, is shown in Table 2, as applied to the system illustrated in FIG. 3.

TABLE 2

| TIME UNIT | COLUMN | | | | |
|---|---|---|---|---|---|
| | A | B | C | D | E |
| I | Ads | RP | P | DP | CDR |
| II | CDR | Ads | RP | P | DP |
| III | DP | CDR | Ads | RP | P |
| IV | P | DP | CDR | Ads | RP |
| V | RP | P | DP | CDR | Ads |

Ads = Adsorption of $CO_2$
CDR = Carbon dioxide rinse
DP = Depressurization
P = Purge with nitrogen
RP = Repressure with PSA effluent As seen in FIG. 3, the five columns are labeled A to E and similar parts are designated by the same reference numerals as in FIG. 2. In addition to the manifolds 10, 20, 40 and 50, means are provided for introduction of $CO_2$ as a rinse gas and for withdrawal of the rinse effluent.

In this embodiment, as in the one previously described, the fuel gas is passed from manifold 10 into and through the on-stream column wherein carbon dioxide and other impurities are adsorbed, while a stream con-

TABLE 1

| COLUMN | | | | VALVE | | | | | | | | | | | | | | | | | | | | Time Period |
|---|---|---|---|---|---|---|---|---|---|---|---|---|---|---|---|---|---|---|---|---|---|---|---|---|
| A | B | C | D | 15 | 16 | 17 | 18 | 31 | 32 | 33 | 34 | 41 | 42 | 43 | 44 | 51 | 52 | 53 | 54 | 61 | 62 | 63 | 64 | |
| Ads | RP | P | DP | o | c | c | c | o | c | c | c | c | c | o | o | c | c | o | c | c | o | c | c | I |
| DP | Ads | RP | P | c | o | c | c | c | c | o | c | c | c | o | c | o | c | c | o | c | c | o | c | II |
| P | DP | Ads | RP | c | c | o | c | c | c | o | c | o | o | c | c | o | c | c | c | c | c | c | o | III |
| RP | P | DP | Ads | c | c | c | o | c | c | c | o | c | o | o | c | c | o | c | c | o | c | c | c | IV |

Ads = Adsorption of $CO_2$
DP = Depressurization
P = Purge with $N_2$ from NRU
RP = Repressure with PSA effluent
o = open
c = closed sisting essentially of methane and nitrogen is being discharged into manifold 20. Following the adsorption step the $CO_2$-laden column is rinsed with carbon dioxide introduced from manifold 65, in the same direction as that of feed introduction. The carbon dioxide used may be from any conveniently available source; for example that recovered as a fuel gas stream leaving a cryogenic unit for separation of $CO_2$ and $CH_4$, such as one employed in treatment of well gas discharged in EOR operation. The $CO_2$-containing rinse effluent is discharged into manifold 66 and recycled to the PSA feed end, joining the fresh feed in manifold 10. Because of the pressure drop in the bed of adsorbent, the carbon dioxide rinse gas must be introduced at a slightly higher pressure in order to permit the recycle of the rinse effluent at the feed gas inlet.

Following the described rinse step the bed is depressurized to lowest possible pressure by gas withdrawal into manifold 70. At the attained low pressure level (~20 psia), nitrogen discharged from the NRU operation is passed through the bed from manifold 50 to purge the $CO_2$ in the bed into manifold 40, from which the purge effluent may be vented to the atmosphere.

Following the purging with nitrogen, the bed is repressured to the designed operating level for repetition of the cycle, starting with adsorption of $CO_2$ from the mixed gas feed. The repressuring is preferably carried out counter to feed direction, employing part of the $CO_2$-freed PSA effluent from manifold 20 recycled via return manifold 30.

By the described five-step operating cycle essentially all of the methane is recovered from the feed gas and very little methane is retained in the bed. If recovery of carbon dioxide is desired, the carbon dioxide discharged from the bed into manifold 70 during depressurizing of the bed, may be collected in a surge tank, as shown at 100 and recompressed for further desired use. If recovery of $CO_2$ is not desired the surge tank 100 and recompression of the depressurization gas may be omitted.

Following the operating schedule set out in Table 2, during the time interval when column A is on the adsorption stroke, column B will be on repressurization, receiving part of the effluent from column A. Thus, all of the valves connected with column A will be closed except for valves 15 and 31, so that the feed gas from manifold 10 enters the column via line 11 and the unsorbed product gas is discharged via line 21 into manifold 20 through which it is charged to the NRU installation. Part of the product flowing through line 20 is withdrawn through line 30, through open valve 62 and passed into column B for repressuring that column; all other valves associated with column B being closed during that time interval. At the termination of the adsorption step in column A, valves 15, 31 and 62 are closed and valves 16 and 32 opened, switching feed introduction into repressured column B. At this time also, valve 71 is opened so that $CO_2$ rinse gas is introduced into column A in feed direction via line 11. The rinse effluent discharged through line 21 is recycled to feed manifold 10 via open valve 81.

In the third time interval (III) column A is depressured by withdrawing its gas content (mostly $CO_2$) into manifold 70 counter to feed direction, by opening valve 86 in manifold 70. As earlier indicated, the withdrawn gas may be vented or collected in surge tank 100.

During the fourth time interval (IV) column A is purged at the low pressure attained during the previous time interval. Thus, nitrogen gas separated from $CH_4$ in the NRU facility, is returned to column A via manifold 50 and open valve 51, the purge effluent being discharged to vent through open valve 91 and manifold 40.

Following the above described purge step valve 91 and valve 51 are closed and column A is repressured to the pressure level employed in adsorption of $CO_2$, for repetition of the described sequence of operations therein. Repressurization is effected by introduction of part of the unsorbed effluent discharged from a companion column undergoing the adsorption step. Thus, in the illustrated embodiment, part of the high pressure gas discharged into manifold 20 from column E is by-passed into column A via manifold 30 and open valve 96. At the completion of the repressuring step, the described cycle sequence of operations is repeated. The same sequence of operations, in turn, is carried out in each of columns A through E, with appropriate opening and closing of the valves associated with the respective columns.

As indicated above, the five-step sequence described in Table 2 is not limited to a system having five columns operated in parallel nor to a system wherein each of the recited steps is performed during an equal time interval. In the five column system of Table 2, each column is on the adsorption step during one-fifth of the time devoted for a complete cycle. The same five step sequence can be arranged to provide a larger proportional time interval of the cycle to adsorption. For example, during a twenty time units cycle, six time units (30%) can be applied to adsorption, four units to $CO_2$ rinse; four units each to depressurize and purge, and two units to repressuring. Such arrangement could be carried out in continuous manner employing ten columns in parallel.

Other cycles using a ten column arrangement can be formulated to provide a longer useful time devoted to the adsorption step, as seen in Table 3.

TABLE 3

| | $CO_2$ Adsorption | Rinse | Depressure | Purge | Repressure |
|---|---|---|---|---|---|
| Time Units | 8 | 2 | 2 | 4 | 4 |
| | 8 | 2 | 2 | 6 | 2 |
| | 6 | 4 | 2 | 6 | 2 |
| | 6 | 6 | 2 | 4 | 2 |

Other possible arrangements for the five step cycle are exemplified by an eight column system (11 time units cycle) in which 6 units are devoted to adsorption, 4 units to purging and 2 units each for $CO_2$ rinse, depressuring and repressuring. In a six column system using an 18 time units cycle, one-third of the cycle time can be usefully employed in adsorption of $CO_2$, the remaining time being equally divided to the regeneration and repressuring steps (3 units each). Another arrangement of a 6 column system operated to provide one-third of the time cycle to adsorption, may employ eight time units for adsorption and four time units each to the regeneration and repressuring steps.

CASE III

Figure 4:
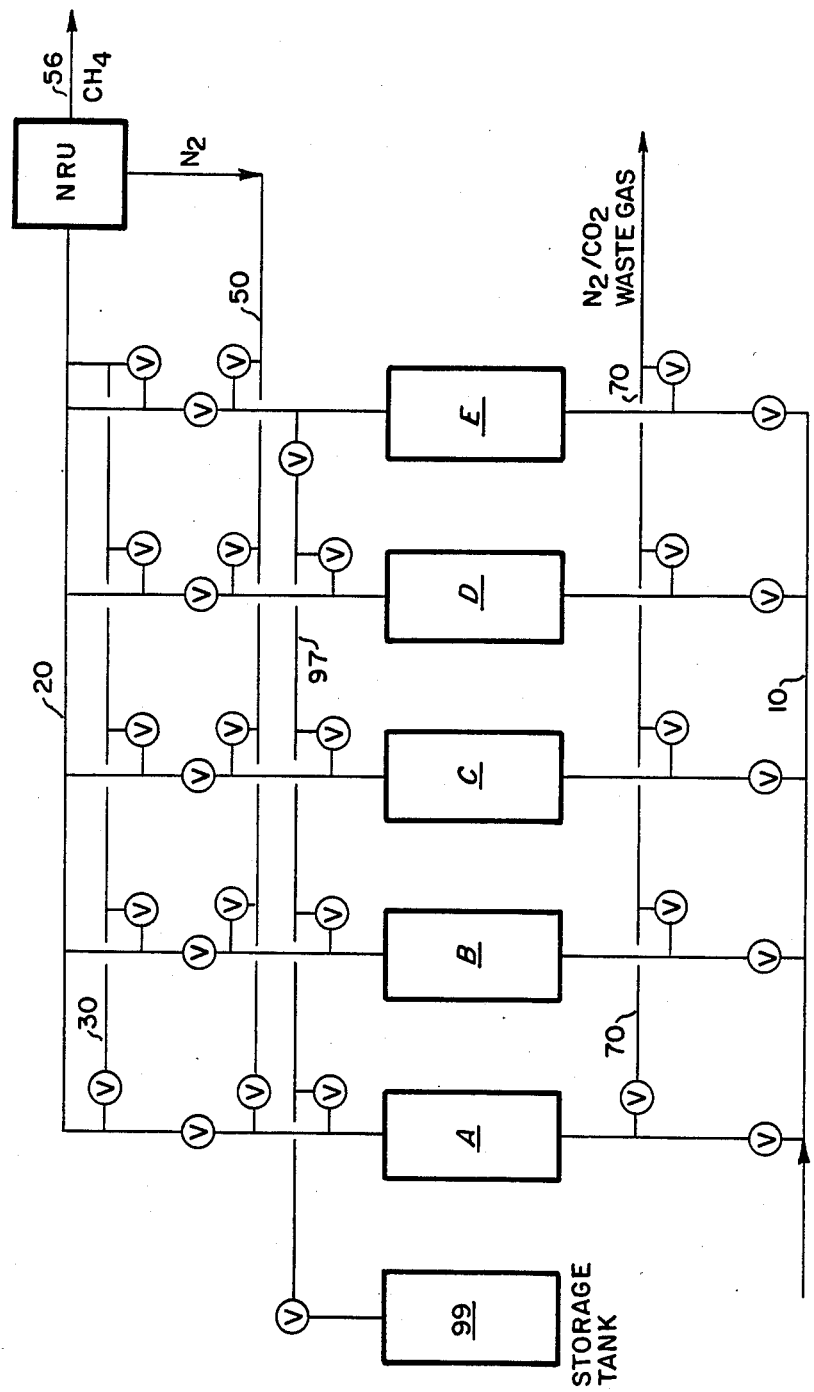

A modified system for practice of the invention is illustrated by the flow diagram in FIG. 4. This alternative embodiment differs from those hereinabove described by the introduction of pressure equalization among companion columns during the cycle. While FIG. 4 shows a five column system, it will be understood that installations having a larger number of parallel columns may be employed with longer or shorter time intervals for each of the steps appropriately arranged. In operation of the system illustrated in FIG. 4, fuel gas is passed, as before, into the on-stream column wherein carbon dioxide and other impurities are adsorbed. At the termination of the adsorption step, the sorbate-laden column (A) undergoes an equalization/depressurization by withdrawal of gas therefrom into a companion column, say column D. Column A then undergoes a second equalization/depressurization by passing gas into storage tank 99 via line 97 as shown in FIG. 4. After the two pressure let-down steps recited, the bed in column A undergoes a further depressurization step via line 70 before the gas from the NRU facility is used via line 50 to purge the adsorbent bed in the column. Following the purge step column A is repressured to equal pressure with a companion column by gas flow from the companion column (say column C) then gas from a holding tank is also used to repressurize and then repressurized to final operating pressure level with PSA effluent by-passed by line 30. Some small loss of methane (~3%) is had in this embodiment because of the void space gas purged.

A typical set of stream flow rates, compositions and pressures for certain designated key streams are outlined in Tables 5, 6 and 7 for the three embodiments above described. The reported figures are based on the treatment of a fuel gas stream having the composition indicated in Table 4.

TABLE 4

| Component | Mole % |
|---|---|
| $CH_4$ | 48.26 |
| $N_2$ | 31.74 |
| $CO_2$ | 19.94 |
| $C_2$ | 0.04 |
| $C_6$ | 0.02 |
| $C_7$ | 22 ppm |

TABLE 5

Selected Flowrates and Pressures for Case 1
Corresponding to Stream Numbers in FIG. 2

| | Stream No. | | | | | |
|---|---|---|---|---|---|---|
| | 10 | 40 | 20 | 50 | 70 | 25 |
| Components (lb moles/hr) | | | | | | |
| $CH_4$ | 432.9 | 47.5 | 385.4 | — | 385.4 | 385.4 |
| $N_2$ | 284.7 | 284.7 | 284.7 | 268.6 | 16.1 | 16.1 |
| $CO_2$ | 178.9 | 178.9 | — | — | — | — |
| $C_2$ | 0.4 | 0.4 | — | — | — | — |
| $C_6$ | 0.2 | 0.2 | — | — | — | — |
| $C_7$ | 0.02 | 0.02 | — | — | — | — |
| Total flow | 897.0 | 511.7 | 670.1 | 268.6 | 401.5 | 401.5 |
| Pressure (psia) | 360 | 20 | 350 | 20 | 100 | 800 |

TABLE 6

Selected Flowrates and Pressures for Case 2
Corresponding to Stream Numbers in FIG. 3

| | Stream No. | | | | |
|---|---|---|---|---|---|
| | 10 | 40 | 20 | 50 | 60 |
| Components (lb moles/hr) | | | | | |
| $CH_4$ | 432.9 | 9.1 | 423.8 | — | 423.8 |
| $N_2$ | 284.7 | 284.7 | 284.7 | 267.0 | 17.7 |
| $CO_2$ | 178.9 | 95.7 | — | — | — |
| $C_2$ | 0.4 | 0.4 | — | — | — |
| $C_6$ | 0.2 | 0.2 | — | — | — |
| $C_7$ | 0.02 | 0.02 | — | — | — |
| Total Flow | 897.0 | 390.1 | 708.5 | 267.0 | 441.5 |
| Pressure (psia) | 360 | 20 | 350 | 20 | 100 |

TABLE 7

Selected Flowrates and Pressures for Case 3
Corresponding to Stream Numbers in FIG. 4

| | Stream No. | | | | |
|---|---|---|---|---|---|
| | 10 | 70 | 20 | 50 | 56 |
| Components (lb moles/hr) | | | | | |
| $CH_4$ | 432.9 | 17.9 | 415.0 | — | 415.0 |
| $N_2$ | 284.7 | 284.7 | 284.7 | 267.4 | 17.3 |
| $CO_2$ | 178.9 | 178.9 | — | — | — |
| $C_2$ | 0.4 | 0.4 | — | — | — |
| $C_6$ | 0.2 | 0.2 | — | — | — |
| $C_7$ | 0.02 | 0.02 | — | — | — |
| Total Flow | 897.0 | 482.1 | 699.7 | 267.4 | 432.3 |
| Pressure (psia) | 360 | 20 | 350 | 20 | 100 |

The time intervals and cycle sequence of a five column system such as that illustrated in FIG. 4 is exemplified in Table 8, operating in a 20 time unit cycle.

TABLE 8

| Time Unit | Column | | | | | 99 Storage |
|---|---|---|---|---|---|---|
| | A | B | C | D | E | |
| 1 | Ads | $ERP_1$/RP | P | $EDP_1$ | Ads | Hold |
| 2 | Ads | RP | P | $EDP_2$ | Ads | Store |
| 3 | Ads | RP | P | DP | Ads | Hold |
| 4 | Ads | RP | $ERP_2$ | P | Ads | Release |
| 5 | Ads | Ads | $ERP_1$/RP | P | $EDP_1$ | Hold |
| 6 | Ads | Ads | RP | P | $EDP_2$ | Store |
| 7 | Ads | Ads | RP | P | DP | Hold |
| 8 | Ads | Ads | RP | $ERP_2$ | P | Release |
| 9 | $EDP_1$ | Ads | Ads | $ERP_1$/RP | P | Hold |
| 10 | $EDP_2$ | Ads | Ads | RP | P | Store |
| 11 | DP | Ads | Ads | RP | P | Hold |
| 12 | P | Ads | Ads | RP | $ERP_2$ | Release |
| 13 | P | $EDP_1$ | Ads | Ads | $ERP_1$/RP | Hold |
| 14 | P | $EDP_2$ | Ads | Ads | RP | Store |
| 15 | P | DP | Ads | Ads | RP | Hold |
| 16 | $ERP_2$ | P | Ads | Ads | RP | Release |
| 17 | $ERP_1$/RP | P | $EDP_1$ | Ads | Ads | Hold |
| 18 | RP | P | $EDP_2$ | Ads | Ads | Store |
| 19 | RP | P | DP | Ads | Ads | Hold |

TABLE 8-continued

| Time | Column | | | | | 99 |
| --- | --- | --- | --- | --- | --- | --- |
| Unit | A | B | C | D | E | Storage |
| 20 | RP | ERP$_2$ | P | Ads | Ads | Release |

EDP$_1$ = Equalization depressurization #1
EDP$_2$ = Equalization depressurization #2
ERP$_1$ = Equalization repressurization #1
ERP$_2$ = Equalization repressurization #2
RP = Repressurization with PSA effluent
Hold = Hold gas in storage tank 99
Store = Admit gas into storage tank 99
Release = Release gas from storage tank 99

The preferred adsorbent for practice of the invention is Linde 13X. Other adsorbents that can be employed for removal of CO$_2$ from a stream containing the same in admixture with methane include Ca X or other similar molecular sieves.

What is claimed:

1. The method of recovering methane from a fuel gas mixture containing also nitrogen and carbon dioxide, which comprises the steps of:
   (a) passing said fuel gas mixture at superatmospheric pressure through a bed of adsorbent wherein carbon dioxide is selectively adsorbed while withdrawing from said bed a stream comprised of unadsorbed components including methane and nitrogen;
   (b) subjecting said stream to cryogenic distillation to separate substantially all of the nitrogen therefrom and recovering as product methane of high purity;
   (c) rinsing said bed of step (a) with a stream of carbon dioxide passed through the bed in a direction cocurrent to that employed in initial introduction of said fuel gas mixture in step (a);
   (d) recycling at least a part of the effluent obtained during said rinse of step (c) as a component of the feed gas mixture subjected to step (a);
   (e) reducing the pressure in the bed of step (a);
   (f) utilizing at least part of the nitrogen separated in step (b) above to purge from the bed carbon dioxide retained therein during step (a); and
   (g) repressurizing said bed of step (a) with a stream of unadsorbed components having the composition of that withdrawn during step (a).

2. The method as defined in claim 1 wherein the carbon dioxide evolved from said bed during said pressure reduction is collected and recompressed.

3. The method as defined in claim 1 wherein said bed of adsorbent is part of a pressure swing adsorption system comprised of five such beds operated in parallel in a fixed time sequence, wherein each of said beds in turn is subjected to the sequence of steps: (1) adsorption of carbon dioxide, (2) rinse with carbon dioxide, (3) pressure reduction, (4) purge with nitrogen and (5) repressuring to adsorption pressure level; each of said steps being performed for a substantially equal time period.

4. The method as defined in claim 1 wherein said fuel gas mixture subjected to selective removal of carbon dioxide is one obtained from enhanced oil recovery operations.

5. The method as defined in claim 1 wherein the recited sequence of steps is carried out in a pressure swing adsorption system comprised of four adsorbent beds operated in parallel during a fixed time period cycle, wherein each of the recited steps occupies a substantially equal time period.

6. The method as defined in claim 1 wherein said adsorbent bed is comprised of 13X molecular sieve.

7. The method as defined in claim 1 wherein said bed of adsorbent is part of a pressure swing adsorbent system comprised of at least five such beds operated in parallel in a fixed time sequence, and wherein following recited step (a) the pressure in the carbon dioxide-laden bed is lowered by passing gas therefrom into one or more companion beds which are at lower pressure level, followed by further removal of gas passed therefrom into a holding receptacle, prior to purging with nitrogen.

8. The method as defined in claim 7 wherein following its purging with nitrogen the bed is brought to the superatmospheric pressure level of step (a) with unadsorbed gas withdrawn from a companion bed during the adsorptioin step performed in said companion bed.

* * * * *